United States Patent
Bedard et al.

(10) Patent No.: US 8,323,354 B2
(45) Date of Patent: *Dec. 4, 2012

(54) INSTRUMENTED PROSTHETIC FOOT

(75) Inventors: Stephane Bedard, Quebec (CA); Pierre-Olivier Roy, Quebec (CA)

(73) Assignee: Victhom Human Bionics Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/436,595

(22) Filed: Mar. 30, 2012

(65) Prior Publication Data

US 2012/0191220 A1    Jul. 26, 2012

Related U.S. Application Data

(60) Continuation of application No. 13/354,188, filed on Jan. 19, 2012, which is a continuation of application No. 11/881,964, filed on Jul. 31, 2007, now abandoned, which is a division of application No. 10/715,989, filed on Nov. 18, 2003, now abandoned.

(51) Int. Cl.
*A61F 2/64* (2006.01)
(52) U.S. Cl. ......................................................... 623/47
(58) Field of Classification Search .................... 623/26, 623/47–56
See application file for complete search history.

(56) References Cited

U.S. PATENT DOCUMENTS

| | | | |
|---|---|---|---|
| 2,568,051 A | 9/1951 | Catranis | |
| 2,619,652 A | 12/1952 | Vesper | |
| 2,859,451 A | 11/1958 | Mauch | |
| 3,316,558 A | 5/1967 | Mortensen | |
| 3,417,409 A | 12/1968 | Prahl | |
| 3,501,776 A | 3/1970 | Beeker et al. | |
| 3,659,294 A | 5/1972 | Glabiszewski | |
| 3,701,368 A | 10/1972 | Stern | |
| 3,791,375 A | 2/1974 | Pfeiffer | |
| 3,820,168 A | 6/1974 | Horvath | |
| 3,866,246 A | 2/1975 | Seamone et al. | |
| 3,871,032 A | 3/1975 | Karas | |
| 3,995,324 A | 12/1976 | Burch | |
| 4,005,496 A | 2/1977 | Wilkes | |

(Continued)

FOREIGN PATENT DOCUMENTS

CA    2405356    10/2001

(Continued)

OTHER PUBLICATIONS

"MT9 Inertial 3D Motion Tracker," Xsens Technologies B.V., available at http://www.xsens.com/download/MT9_brochure.pdf (at least as early as Oct. 2004), printed Jul. 20, 2006.

(Continued)

*Primary Examiner* — William H. Matthews
(74) *Attorney, Agent, or Firm* — Knobbe Martens Olson & Bear, LLP

(57) ABSTRACT

The present invention discloses an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

7 Claims, 15 Drawing Sheets

U.S. PATENT DOCUMENTS

| | | |
|---|---|---|
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,094,086 A | 6/1978 | Gevers |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,370,977 A | 2/1983 | Mauldin et al. |
| 4,386,891 A | 6/1983 | Riefel et al. |
| 4,387,472 A | 6/1983 | Wilson |
| 4,441,644 A | 4/1984 | Farian |
| 4,458,367 A | 7/1984 | May |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,602,619 A | 7/1986 | Wolf et al. |
| 4,617,920 A | 10/1986 | Carsalade |
| 4,649,934 A | 3/1987 | Fraser et al. |
| 4,657,000 A | 4/1987 | Hepburn |
| 4,685,926 A | 8/1987 | Haupt |
| 4,685,927 A | 8/1987 | Haupt |
| 4,711,242 A | 12/1987 | Petrofsky |
| 4,711,450 A | 12/1987 | McArthur |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Roung et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,854,428 A | 8/1989 | Horvath |
| 4,865,024 A | 9/1989 | Hensley et al. |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,994,086 A | 2/1991 | Edwards |
| 5,020,790 A | 6/1991 | Beard et al. |
| 5,033,291 A | 7/1991 | Podoloff et al. |
| 5,044,360 A | 9/1991 | Janke |
| 5,062,856 A | 11/1991 | Sawamura et al. |
| 5,062,857 A | 11/1991 | Berringer |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A * | 4/1993 | Maxwell .................. 623/24 |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,253,656 A | 10/1993 | Rincoe et al. |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnäs |
| 5,323,650 A | 6/1994 | Fullen et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnas |
| 5,376,137 A | 12/1994 | Shorter et al. |
| 5,382,373 A | 1/1995 | Carlson et al. |
| 5,383,939 A | 1/1995 | James |
| 5,397,287 A | 3/1995 | Lindfors |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts et al. |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,472,412 A | 12/1995 | Knoth |
| 5,476,441 A | 12/1995 | Durfee et al. |
| 5,504,415 A | 4/1996 | Podrazhansky et al. |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,568 A | 9/1998 | Atkinson et al. |
| 5,810,752 A | 9/1998 | Grifka |
| 5,823,309 A | 10/1998 | Gopalswamy et al. |
| 5,842,547 A | 12/1998 | Carlson et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allen |
| 5,929,332 A | 7/1999 | Brown |
| 5,941,913 A | 8/1999 | Woolnough et al. |
| 5,947,238 A | 9/1999 | Jolly et al. |
| 5,948,021 A | 9/1999 | Radcliffe |
| 5,955,667 A | 9/1999 | Fyfe |

| | | | | | | |
|---|---|---|---|---|---|---|
| 5,957,981 | A | 9/1999 | Gramnas | 6,811,571 B1 | 11/2004 | Phillips |
| 5,960,918 | A | 10/1999 | Moser et al. | 6,813,582 B1 | 11/2004 | Levi et al. |
| 5,967,273 | A | 10/1999 | Hampton | D499,487 S | 12/2004 | Bedard et al. |
| 5,972,035 | A | 10/1999 | Blatchford | D501,925 S | 2/2005 | Bedard et al. |
| 5,982,156 | A | 11/1999 | Weimer et al. | 6,855,170 B2 | 2/2005 | Gramnas |
| 5,998,930 | A | 12/1999 | Upadhyay et al. | 6,875,241 B2 | 4/2005 | Christensen |
| 6,006,412 | A | 12/1999 | Bergmann et al. | 6,876,135 B2 | 4/2005 | Pelrine et al. |
| 6,007,582 | A | 12/1999 | May | 6,918,308 B2 | 7/2005 | Biedermann |
| RE36,521 | E | 1/2000 | Hiemisch | 6,955,692 B2 | 10/2005 | Grundei |
| 6,039,091 | A | 3/2000 | Rodgers et al. | 6,966,882 B2 | 11/2005 | Horst |
| 6,061,577 | A | 5/2000 | Andrieu et al. | 6,966,933 B2 | 11/2005 | Christensen |
| 6,080,123 | A | 6/2000 | Pansiera | 7,025,792 B2 | 4/2006 | Collier |
| 6,086,616 | A | 7/2000 | Okuda et al. | 7,029,500 B2 * | 4/2006 | Martin .................. 623/50 |
| 6,091,977 | A * | 7/2000 | Tarjan et al. .................. 600/372 | 7,042,197 B2 | 5/2006 | Turner et al. |
| 6,093,162 | A | 7/2000 | Fairleigh et al. | 7,063,727 B2 | 6/2006 | Phillips et al. |
| 6,095,486 | A | 8/2000 | Ivers et al. | 7,066,896 B1 | 6/2006 | Kiselik |
| 6,113,642 | A | 9/2000 | Petrofsky et al. | 7,101,487 B2 | 9/2006 | Hsu et al. |
| 6,117,177 | A | 9/2000 | Chen et al. | 7,118,601 B2 | 10/2006 | Yasui et al. |
| 6,129,690 | A | 10/2000 | Hamlin et al. | 7,131,998 B2 | 11/2006 | Pasolini |
| 6,129,766 | A | 10/2000 | Johnson et al. | 7,137,998 B2 | 11/2006 | Bedard |
| 6,139,586 | A | 10/2000 | Wagner et al. | 7,147,667 B2 | 12/2006 | Bedard |
| 6,151,624 | A | 11/2000 | Teare et al. | 7,164,967 B2 | 1/2007 | Etienne-Cummings et al. |
| 6,164,967 | A | 12/2000 | Sale | 7,198,071 B2 | 4/2007 | Bisbee, III et al. |
| 6,165,226 | A | 12/2000 | Wagner | 7,308,333 B2 | 12/2007 | Kern et al. |
| 6,168,634 | B1 | 1/2001 | Schmitz | 7,313,463 B2 | 12/2007 | Herr et al. |
| 6,183,425 | B1 | 2/2001 | Whalen et al. | 7,314,490 B2 | 1/2008 | Martin |
| 6,185,614 | B1 | 2/2001 | Cuomo et al. | 7,393,364 B2 | 7/2008 | Martin |
| 6,187,051 | B1 | 2/2001 | Gerad van de Veen | 7,410,338 B2 | 8/2008 | Schiele et al. |
| 6,195,921 | B1 | 3/2001 | Truong | 7,410,471 B1 | 8/2008 | Campbell et al. |
| 6,206,932 | B1 | 3/2001 | Johnson | 7,431,737 B2 | 10/2008 | Ragnarsdottir et al. |
| 6,206,933 | B1 | 3/2001 | Shorter et al. | 7,455,696 B2 | 11/2008 | Bisbee, III et al. |
| 6,206,934 | B1 | 3/2001 | Phillips | 7,462,201 B2 | 12/2008 | Christensen |
| 6,241,775 | B1 | 6/2001 | Blatchford | 7,503,900 B2 | 3/2009 | Goswami |
| 6,301,964 | B1 | 10/2001 | Fyfe et al. | 7,520,904 B2 | 4/2009 | Christensen |
| 6,342,076 | B1 | 1/2002 | Lundborg | 7,531,006 B2 | 5/2009 | Clausen et al. |
| 6,350,286 | B1 | 2/2002 | Atkinson et al. | 7,575,602 B2 | 8/2009 | Amirouche et al. |
| 6,352,144 | B1 | 3/2002 | Brooks | 7,637,957 B2 | 12/2009 | Ragnarsdottir et al. |
| 6,361,570 | B1 | 3/2002 | Gow | 7,637,959 B2 | 12/2009 | Clausen et al. |
| 6,373,152 | B1 | 4/2002 | Wang et al. | 7,641,700 B2 | 1/2010 | Yasui |
| 6,395,193 | B1 | 5/2002 | Kintz et al. | 7,655,050 B2 | 2/2010 | Palmer et al. |
| 6,409,695 | B1 | 6/2002 | Connelly | 7,736,394 B2 | 6/2010 | Bédard et al. |
| 6,423,098 | B1 | 7/2002 | Biedermann | 7,794,505 B2 | 9/2010 | Clausen et al. |
| 6,425,925 | B1 | 7/2002 | Grundei | 7,811,333 B2 | 10/2010 | Jonsson et al. |
| 6,430,843 | B1 | 8/2002 | Potter et al. | 7,811,334 B2 | 10/2010 | Ragnarsdottir et al. |
| 6,436,149 | B1 | 8/2002 | Rincoe | 7,815,689 B2 | 10/2010 | Bedard et al. |
| 6,443,993 | B1 | 9/2002 | Koniuk | 7,862,620 B2 | 1/2011 | Clausen et al. |
| 6,443,995 | B1 | 9/2002 | Townsend et al. | 7,867,284 B2 | 1/2011 | Bedard |
| 6,451,481 | B1 | 9/2002 | Lee et al. | 7,867,285 B2 | 1/2011 | Clausen et al. |
| 6,485,519 | B2 | 11/2002 | Meyers et al. | 7,896,927 B2 | 3/2011 | Clausen et al. |
| 6,494,039 | B2 | 12/2002 | Pratt et al. | 7,918,808 B2 | 4/2011 | Simmons |
| 6,500,210 | B1 | 12/2002 | Sabolich et al. | 7,942,935 B2 | 5/2011 | Iversen et al. |
| 6,513,381 | B2 | 2/2003 | Fyfe et al. | 7,955,398 B2 * | 6/2011 | Bedard et al. .................. 623/53 |
| 6,517,585 | B1 | 2/2003 | Zahedi et al. | 8,007,544 B2 | 8/2011 | Jonsson et al. |
| 6,517,828 | B1 | 2/2003 | Le Moel et al. | 8,048,172 B2 | 11/2011 | Jonsson et al. |
| 6,522,266 | B1 | 2/2003 | Soehren et al. | 8,057,550 B2 | 11/2011 | Clausen |
| 6,537,322 | B1 | 3/2003 | Johnson et al. | 8,075,633 B2 | 12/2011 | Herr et al. |
| 6,574,655 | B1 | 6/2003 | Libert et al. | 8,083,807 B2 | 12/2011 | Auberger et al. |
| 6,587,728 | B2 | 7/2003 | Fang et al. | 8,087,498 B2 | 1/2012 | Dupuis et al. |
| 6,589,287 | B2 | 7/2003 | Lundborg | 8,122,772 B2 | 2/2012 | Clausen et al. |
| 6,599,439 | B2 | 7/2003 | Iyengar et al. | 2002/0087216 A1 | 7/2002 | Atkinson et al. |
| 6,602,295 | B1 | 8/2003 | Doddroe et al. | 2003/0019700 A1 | 1/2003 | Wittig |
| 6,610,101 | B2 | 8/2003 | Herr et al. | 2003/0120353 A1* | 6/2003 | Christensen .................. 623/26 |
| 6,613,097 | B1 | 9/2003 | Cooper | 2004/0064195 A1 | 4/2004 | Herr |
| 6,645,252 | B2 | 11/2003 | Asai et al. | 2004/0083007 A1 | 4/2004 | Molino et al. |
| 6,663,673 | B2 | 12/2003 | Christensen | 2004/0111163 A1 | 6/2004 | Bedard et al. |
| 6,671,531 | B2 | 12/2003 | Al-Ali et al. | 2004/0215111 A1 | 10/2004 | Bonutti et al. |
| 6,679,920 | B2 | 1/2004 | Biedermann et al. | 2005/0010139 A1 | 1/2005 | Aminian et al. |
| 6,695,885 | B2 | 2/2004 | Schulman et al. | 2005/0107889 A1 | 5/2005 | Bedard et al. |
| 6,719,806 | B1 | 4/2004 | Zahedi et al. | 2005/0137717 A1 | 6/2005 | Gramnas et al. |
| 6,733,180 | B2 | 5/2004 | Nakamura | 2005/0216097 A1 | 9/2005 | Rifkin |
| 6,740,123 | B2 | 5/2004 | Davalli et al. | 2006/0122711 A1 | 6/2006 | Bedard et al. |
| 6,740,125 | B2 | 5/2004 | Mosler | 2006/0173552 A1 | 8/2006 | Roy |
| 6,743,260 | B2 | 6/2004 | Townsend et al. | 2006/0184252 A1 | 8/2006 | Oddsson et al. |
| 6,755,870 | B1 | 6/2004 | Biedermann et al. | 2006/0184280 A1 | 8/2006 | Oddsson et al. |
| 6,761,743 | B1 | 7/2004 | Johnson | 2006/0249315 A1 | 11/2006 | Herr et al. |
| 6,764,520 | B2 | 7/2004 | Deffenbaugh et al. | 2007/0027557 A1 | 2/2007 | Jonsson et al. |
| 6,770,045 | B2 | 8/2004 | Naft et al. | 2007/0043449 A1 | 2/2007 | Herr et al. |
| 6,780,343 | B2 | 8/2004 | Hata et al. | 2007/0050047 A1 | 3/2007 | Ragnarsdottlr et al. |
| 6,805,677 | B2 | 10/2004 | Simmons | 2007/0123997 A1 | 5/2007 | Herr et al. |

| | | | |
|---|---|---|---|
| 2007/0162152 A1 | 7/2007 | Herr et al. | |
| 2008/0046096 A1 | 2/2008 | Bedard et al. | |
| 2009/0265018 A1 | 10/2009 | Goldfarb et al. | |
| 2009/0299480 A1 | 12/2009 | Gilbert et al. | |
| 2010/0131101 A1 | 5/2010 | Engeberg et al. | |
| 2010/0160844 A1 | 6/2010 | Gilbert et al. | |
| 2010/0262260 A1 | 10/2010 | Bédard et al. | |
| 2010/0305716 A1 | 12/2010 | Pusch et al. | |
| 2010/0324456 A1 | 12/2010 | Jónsson et al. | |
| 2011/0106274 A1 | 5/2011 | Ragnarsdottir et al. | |
| 2011/0125290 A1 | 5/2011 | Langlois | |
| 2011/0130847 A1 | 6/2011 | Bedard et al. | |
| 2011/0137429 A1 | 6/2011 | Bedard | |
| 2011/0224804 A1 | 9/2011 | Clausen et al. | |
| 2011/0245931 A1 | 10/2011 | Clausen et al. | |
| 2012/0016492 A1 | 1/2012 | Clausen | |

FOREIGN PATENT DOCUMENTS

| | | |
|---|---|---|
| CA | 2494365 | 3/2004 |
| CA | 2543061 | 6/2005 |
| CH | 543277 | 12/1973 |
| CN | 2043873 | 9/1989 |
| CN | 1215614 | 5/1999 |
| CN | 2400072 Y | 10/2000 |
| DE | 3543291 | 6/1987 |
| DE | 3923056 | 1/1991 |
| DE | 3923057 | 1/1991 |
| DE | 4305213 | 8/1993 |
| DE | 4318901 | 1/1994 |
| DE | 42 29 330 | 3/1994 |
| EP | 0503775 | 9/1992 |
| EP | 0 549 855 | 7/1993 |
| EP | 0549855 | 7/1993 |
| EP | 0628296 | 12/1994 |
| EP | 0654254 | 5/1995 |
| EP | 0718951 | 6/1996 |
| EP | 0902547 | 3/1999 |
| EP | 1 066 793 | 1/2001 |
| EP | 1125825 | 1/2001 |
| EP | 1107420 | 6/2001 |
| EP | 1 166 726 | 1/2002 |
| EP | 1166726 | 1/2002 |
| EP | 1169982 | 1/2002 |
| EP | 1417942 | 5/2004 |
| FR | 2293185 | 7/1976 |
| FR | 2623086 | 11/1987 |
| FR | 2 623 086 | 5/1989 |
| FR | 2816463 | 5/2002 |
| GB | 2 201 260 | 8/1988 |
| GB | 2 244 006 | 11/1991 |
| GB | 2 260 495 | 4/1993 |
| GB | 2 268 070 | 1/1994 |
| GB | 2 301 776 | 12/1996 |
| GB | 2 302 949 | 2/1997 |
| GB | 2 334 891 | 9/1999 |
| GB | 2 338 653 | 12/1999 |
| GB | 2 343 848 | 5/2000 |
| GB | 2 367 753 | 4/2002 |
| JP | 59/32453 | 2/1984 |
| JP | 59/71747 | 4/1984 |
| JP | 60081530 | 5/1985 |
| JP | 03-181633 | 8/1991 |
| JP | 04-78337 | 3/1992 |
| JP | 5-161668 | 6/1993 |
| JP | 11056885 | 3/1999 |
| JP | 11000345 | 6/1999 |
| JP | 11-215793 | 8/1999 |
| JP | 2001/277175 | 10/2001 |
| JP | 2002/191654 | 7/2002 |
| JP | 2003/250824 | 9/2003 |
| KR | 2002/0041137 | 6/2002 |
| WO | WO 94/06374 | 3/1994 |
| WO | WO 95/26171 | 10/1995 |
| WO | WO 96/39110 | 12/1996 |
| WO | WO 96/41599 | 12/1996 |
| WO | WO 97/00661 | 1/1997 |
| WO | WO 97/27822 | 8/1997 |
| WO | WO 98/38951 | 9/1998 |
| WO | WO 99/00075 | 1/1999 |
| WO | WO 99/05991 | 2/1999 |
| WO | WO 99/55261 | 11/1999 |
| WO | WO 00/27318 | 5/2000 |
| WO | WO 01/17466 | 3/2001 |
| WO | WO 02/080825 | 10/2002 |
| WO | WO 03/003953 | 1/2003 |
| WO | WO 03/088373 | 10/2003 |
| WO | WO 2004/017872 | 3/2004 |
| WO | WO 2004/092606 | 10/2004 |
| WO | WO 2005/048887 | 6/2005 |
| WO | WO 2006/024876 | 3/2006 |
| WO | WO 2011/100117 | 8/2011 |
| WO | WO 2011/100118 | 8/2011 |

OTHER PUBLICATIONS

Blaya, et al., "Adaptive Control of a Variable-Impedance Ankle-Foot Orthosis to Assist Drop-Foot Gait," IEEE Transactions on Neural Systems and Rehabilitation Engineering, vol. 12, No. 1; pp. 24-31, Mar. 2004.

Blaya, Force-Controllable Ankle Foot Orthosis (AFO) to Assist Drop Foot Gait, Feb. 2003 (believed to be catalogued on or after Jul. 8, 2003).

Blumentritt, Siegmar, Ph.D., et al., Design Principles, Biomedical Data and Clinical Experience With a Polycentric Knee Offering Controlled Stance Phase Knee Flexion: A Preliminary Report, Journal of Prosthetics and Orthotics, 1997, vol. 1, Issue 9, pp. 18-24.

Dietl, H., Der Einsatz von Elektronik bei Prothesen zur Versorgung der unteren Extremitat, Med. Orth. Tech 117 (1997)31-35.

Elliott, Scott B., MR Microprocessor-Controlled Swing and Stance, Presentation to American Academy of Orthotists & Prosthetists, Feb. 4, 2004.

Flowers, et al., Journal of Biomechanical Engineering: Transactions of the ASME; Feb. 1977, pp. 3-8.

Gelat, Thierry et al., Adaptation of the gait initiation process for stepping on to a new level using a single step, Exp Brain Res (2000) 133:538-546, Jun. 21, 2000, pp. 9.

Gronqvist, Raoul et al., Human-centered approaches in slipperiness measurement, Ergonomics, Oct. 20, 2001, vol. 44, Issue 13, pp. 1167-1199 (32 pages).

Hanson, James P. et al., Predicting slips and falls considering required and available friction, Ergonomics, 1999, vol. 42, Issue 12, pp. 1619-1633 (15 pages).

Herr, et al., "User-adaptive control of a magnetorheological prosthetic knee", Industrial Robot: an International Journal, vol. 30, No. 1, (2003) pp. 42-55.

Herr, et al., Patient-Adaptive Prosthetic and Orthotic Leg Systems, 12th Nordic Baltic Conference on Biomedical Engineering and Medical Physics, Proceedings of the International Federation for Medical & Biological Engineering, 2002.

Hill, Stephen W. et al., Altered kinetic strategy for the control of swing limb elevation over obstacles in unilateral below-knee amputee gait, Journal of Biomechanics, 1999, vol. 32, pp. 545-549 (5 pages).

Jones, S. F. et al., The gait initiation process in unilateral lower-limb amputees when stepping up and stepping down to a new level, Clinical Biomechanics, 2005, vol. 20, pp. 405-413 (9 pages).

Kirsner, Scott, A Step in the Right Direction Biomedical Horizons Expanding, Boston Globe, Mar. 17, 2003.

Kuster, M., et al., Kinematic and kinetic comparison of downhill and level walking, Clinical Biomechanics, 1995, vol. 10, Issue 2, pp. 79-84 (6 pages).

Michel, V. et al., The strategies to regulate and to modulate the propulsive forces during gait initiation in lower limb amputees, Exp Brain Res, May 27, 2004, vol. 158, pp. 356-365 (10 pages).

Moseley, Anne M. et al., High- and low-ankle flexibility and motor task performance, Gait and Posture, 2003, vol. 18, pp. 73-80 (8 pages).

Nadeau, S. et al., Frontal and sagittal plane analyses of the stair climbing task in healthy adults aged over 40 years: what are the challenges compared to level walking?, Clinical Biomechanics, 2003, vol. 18, pp. 950-959 (10 pages).

Otto Bock Orthopadische Industrie, C-Leg A new dimension in amputee mobility, Otto Bock Data Sheet, 1997.

Otto Bock Orthopadische Industrie, The Electronic C-Leg Compact Leg Prosthesis System: Instructions for Use, 2002.

Otto Bock Orthopadische Industrie, The Electronic C-Leg Knee Joint System: Instructions for Use, available at http://www.ottobockus.com/products/lower_limb_prosthetics/c-leg_instructions.pdf, 32 pages (printed Jul. 20, 2006).

Popovik, D., et al., Optimal Control for an Above-Knee Prosthesis With Two Degrees of Freedom, J. Biomechanics, 1995, vol. 1, Issue 28, pp. 89-98.

Powers, Christopher M. et al., Stair ambulation in persons with transtibial amputation: An analysis of the Seattle LightFootTM, Journal of Rehabilitation Research and Development, Jan. 1997, vol. 34, Issue 1, pp. 9-18 (10 pages).

Rao, Sreesha S. et al., Segment Velocities in Normal and Transtibial Amputees: Prosthetic Design Implications, IEEE Transactions on Rehabilitation Engineering, Jun. 1998, vol. 6, Issue 2, pp. 219-226 (8 pages).

Redfern, Mark S. et al., Biomechanics of descending ramps, Gait and Posture, 1997, vol. 6, pp. 119-125 (7 pages).

Reiner, Robert et al., Stair ascent and descent at different inclinations, Gait and Posture, 2002, vol. 15, pp. 32-44 (13 pages).

State-Of-The Art Prosthetic Leg Incorporates Magneto-Rheological Technology, Medical Product Manufacturing News, Nov. 2000, pp. 42.

Suga, T., et al., "Newly designed computer controlled knee-ankle-foot orthosis (Intelligent Orthosis)", Prosthetics and Orthotics International, 1998, 22, 230-239.

Thakkar, Sneha, Energy Economy Gait Analysis of an Autoadaptive Prosthetic Knee, Master's Thesis submitted to the Dept. of Electrical Engineering and Computer Science, MIT, Dept. of Electrical Engineering and Computer Science, MIT, 2002, pp. 1-58.

Townsend M A et al., "Biomechanics and modeling of bipedal climbing and descending." Journal of Biomechanics 1976, vol. 9, No. 4, pp. 227-239, XP008078405.

Van Der Loos, H.F.M., et al, ProVAR Assistive Robot System Architecture, Proceedings of the 1999 IEEE International Conference on Robotics & Automation; Detroit, Michigan, May 1999.

Wilkenfeld, Ari Ph.D., et al., An Auto-Adaptive External Knee Prosthesis, Artificial Intelligence Laboratory, MIT, Cambridge, Massachusetts, Sep. 2000, pp. 3.

Wilkenfeld, Ari, Ph.D., Biologically inspired autoadaptive control of a knee prosthesis, Dissertation Abstract, MIT, Cambridge, Massachusetts, Sep. 2000, pp. 1.

Advanced Materials & Processes, Sep. 2003, vol. 9, Issue 161, pp. 29-30, 3 pages.

Carlson, J. David, What makes a Good MR Fluid?, 8th International Conference on Electrorheological (ER) Fluids and magnetorheological (MR) Suspensions, Nice 7 pages, Jul. 9-13, 2001.

Claiborne Jr., C.J., "Making Inodes Behave,", Linux Journal, Publ. by SSC Inc, USA, Feb. 2001, No. 82, pp. 94-99.

Copes/Bionic Ankle, The Most Significant Development in Ankle Prosthetics in Over a Half Century, 1985.

Grimes, Donald L., An Active Multi-Mode Above-Knee Prosthesis Controller, Massachusetts Institute of Technology 1979, 158 pages, 1979.

Herr, Hugh, Presentation at "Experiencing the Frontiers of Biomedical Technology," (Mar. 10-11, 2003).

LeFebvre, W., "Permissions and Access Control Lists", UNIX Review's Performance Computing, Publ. by Miller Freeman, USA, Oct. 1998, vol. 16, No. 11, pp. 59-61.

Namespaces in XML, World Wide Web Consortium Working Draft Sep. 16, 1998; Tim bray (Textuality); Dave Hollander (Hewlett-Packard Company); Andrew Layman (Microsoft).

Otto Bock Orthopadische Industrie GMBH & Co., C-Leg Fitting Statistics (Abstract), Mar. 2000, 4 pages.

Otto, Judith, "Prosthetic Knees: What's on the Way?", The O&P edge, http://www.oandp.com/edge/issues/ articles/2003 -10_02 .asp, Oct. 2003, 5 pages.

Otto, Judith, "Prosthetic Knees: What's Currently New and Impressive?", The O&P Edge, http://www.oandp.com/edge/issues/articles/2003-10_03.sp, Oct. 2003, 4 pages.

R. Tomovic et al., *A Finite State Approach to the Synthesis of Bioengineering Control Systems*, IEEE Transactions on Human Factors in Electronics, vol. HFE-7, No. 2, Jun. 1966.

Kamiar Aminian et al., *Estimation of Speed and Incline of Walking Using Neural Network*, IEEE Transactions on Instrumentation and Measurement, vol. 44, No. 3, Jun. 1995, at 743.

Dejan Popovic et al., Control Aspects of Active Above-Knee Prosthesis, International Journal of Man-Machine Studies, vol. 35, Issue 6, Dec. 1991, at 751.

A. Nakagawa, Intelligent Knee Mechanism and the Possibility to Apply the Principle to the Other Joints, Engineering in Medicine and Biology Society, Proceedings of the 20th Annual International Conference of the IEEE, vol. 20, No. 5, Dec. 1998, at 2282.

Peter H. Veltink et al. (1993), The Feasibility of Posture and Movement Detection by Accelerometry, in 15th Annual International Conference of the IEEE Engineering in Medicine and Biology Society, Oct. 28-31, 1993, San Diego, CA, 1230-1231.

U.S. Appl. No. 60/371,974 to Martin, filed Apr. 12, 2002 (from which U.S. Patent No. 7,029,500, previously submitted, claims priority).

\* cited by examiner

INSTRUMENTED PROSTHETIC FOOT

CROSS-REFERENCE TO RELATED APPLICATIONS

The present application is a continuation of U.S. patent application Ser. No. 13/354,188, filed 19 Jan. 2012, and entitled "INSTRUMENTED PROSTHETIC FOOT", which is a continuation of U.S. patent application Ser. No. 11/881,964, filed 31 Jul. 2007 and now abandoned, which is a divisional application of U.S. patent application Ser. No. 10/715,989, filed 18 Nov. 2003 and now abandoned, each of which is incorporated herein by reference in its entirety and is to be considered a part of this specification.

BACKGROUND

1. Field

The present invention relates to a prosthetic foot for use with a control system and/or a method for controlling an actuated leg prosthesis.

2. Background

As is well known to control engineers, the automation of complex mechanical systems is not something easy to achieve. Among such systems, conventional powered artificial limbs are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional prostheses do not have the capability to interact simultaneously with the human body and the external environment in order to have minimal appropriate functioning.

Accordingly, it is an object of the present application to obviate or mitigate some or all of the above disadvantages.

SUMMARY

According to the present invention, there is provided an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

BRIEF DESCRIPTION OF THE DRAWINGS

Embodiments of the invention will be described by way of example only with reference to the accompanying drawings, in which.

DETAILED DESCRIPTION

The appended figures show a instrumented prosthetic foot (20) having sensors (22A, 22B) for use, in cooperation with possible additional sensors (24A, 24B, 26), with a control system (100) for controlling a prosthesis (14) having an actuating mechanism (16). It should be understood that the present invention is not limited to the illustrated implementation since various changes and modifications may be effected herein without departing from the scope of the appended claims.

Figure 1:
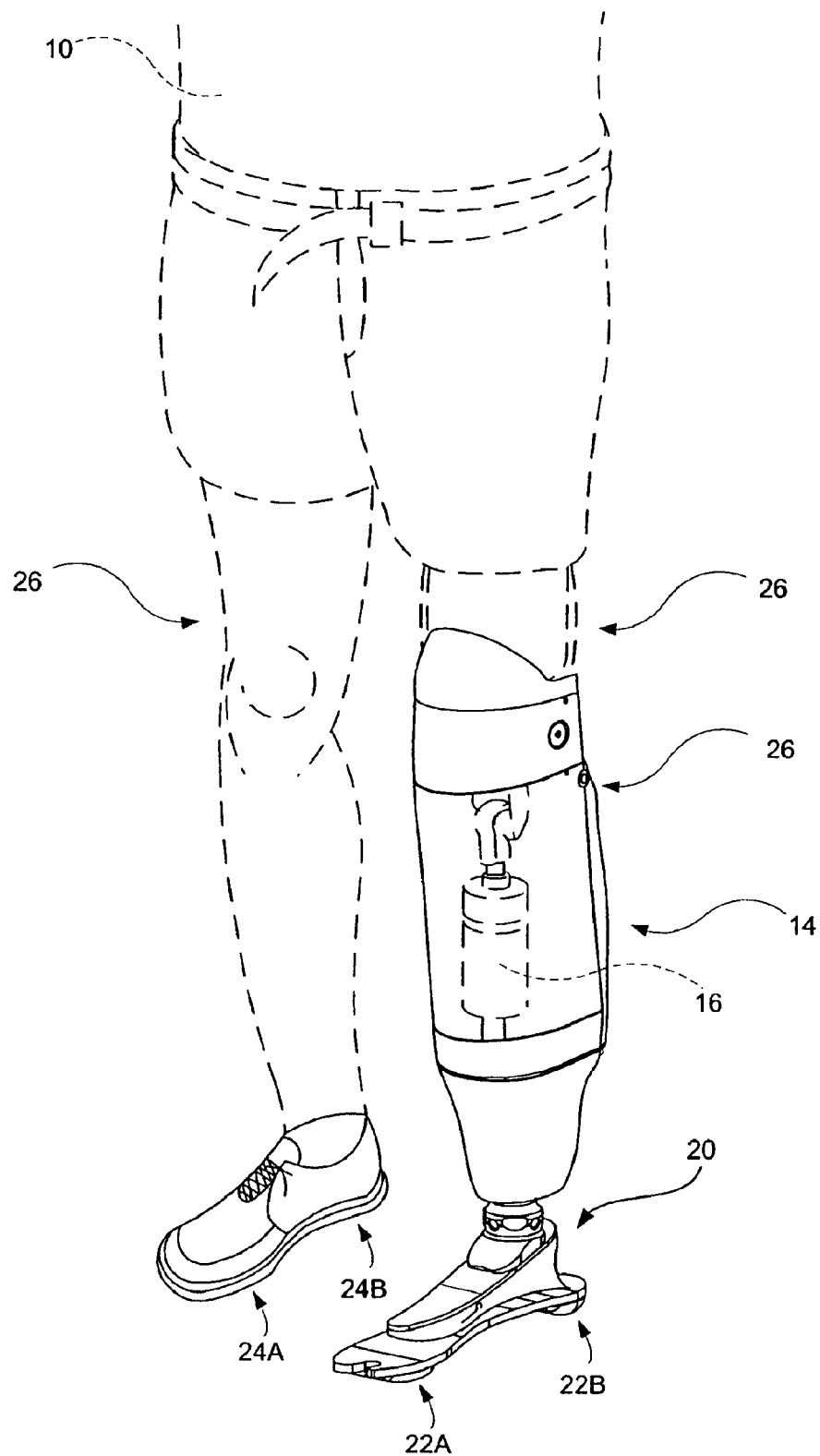
FIG. 1 shows the lower body of an individual provided with a prosthesis and an instrumented prosthetic foot on one side and having a healthy leg on the other side

Referring therefore to FIG. 1 an individual (10) has a pair of legs (26) and (28), one of which, (26), is amputated above the knee. A prosthesis (14) is attached to the leg (26) and includes an actuating mechanism (16), which may be either passive or active. An instrumented prosthetic foot (20) is attached to the prosthesis (14) and includes sensors (22A, 22B). Additional sensors (24A, 24B) are located on the healthy foot and additional sensors (26) located on the individual (10) and/or the prosthesis (14). A passive actuating mechanism may be generally defined as an electromechanical component that only absorbs mechanical energy in order to modify dynamics of mechanical joints of the prosthesis, while an active actuating mechanism may be generally defined as an electromechanical component that absorbs and supplies mechanical energy in order to set dynamics of mechanical joints of the prosthesis.

An example of a passive actuating mechanism is described in U.S. patent application Ser. No. 09/767,367, filed Jan. 22, 2001, entitled "ELECTRONICALLY CONTROLLED PROSTHETIC KNEE". Examples of active actuating mechanisms are described in U.S. patent application Ser. No. 10/463,495 filed Jun. 17, 2003, entitled "ACTUATED PROSTHESIS FOR ABOVE-KNEE AMPUTEES", by Stephane Bedard et al., the entire disclosure of which is hereby incorporated by reference herein.

Figure 2:
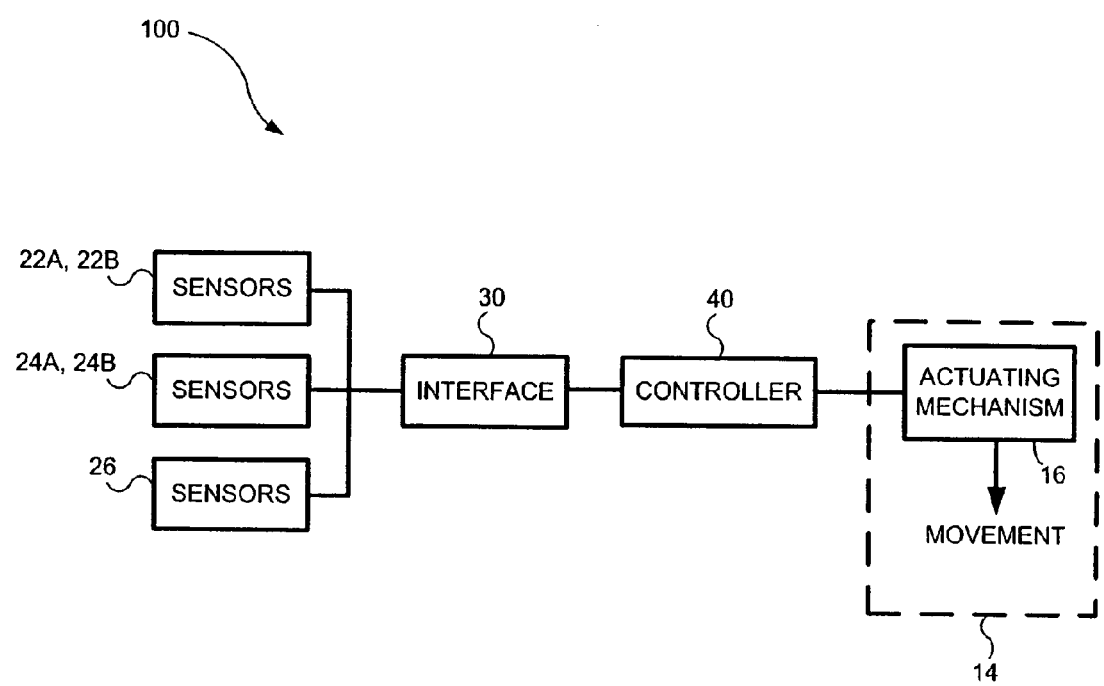
FIG. 2 is a block diagram showing a control system for a prosthesis having an actuating mechanism.

The prosthesis (14) is controlled, as shown schematically in FIG. 2, by a basic control system (100) comprising sensors (22A, 22B, 24A, 24B, 26), connected through an interface (30) to a controller (40). The controller (40) provides signals to an actuating mechanism (16) in the prosthesis (14), such as shown in FIG. 1. The purpose of the control system (100) is to provide the required signals for controlling the actuating mechanism (16). To do so, the control system (100) is interfaced with the amputee (10) using sensors (22A, 22B, 24A, 24B, 26) to ensure proper coordination between the amputee (10) and the movements of the prosthesis (14). The sensors (22A, 22B, 24A, 24B, 26) capture information, in real time, about the dynamics of the amputee's movement and provide that information to the controller (40) via the interface (30). The controller (40) then uses the information to determine the resistance to be applied to a joint, in the case of a passive actuating mechanism, or the joint trajectories and the required angular force or torque that must be applied by a joint, in the case of an active actuating mechanism, in order to provide coordinated movements.

The sensors (22A, 22B, 24A, 24B, 26) may include myoelectric sensors, neuro-sensors, kinematic sensors, kinetic sensors, strain gauges or plantar pressure sensors. Myoelectric sensors are electrodes used to measure the internal or the external myoelectrical activity of skeletal muscles. Neuro-sensors are electrodes used to measure the summation of one or more action potentials of peripheral nerves. Kinematic sensors are used to measure the position of articulated joints, the mobility speed or acceleration of lower extremities. Kinetic sensors are used to measure angular forces at articulated joints or reaction forces of lower extremities. Strain gages are used to measure the strain forces at a specific underfoot area. Plantar pressure sensors are used to measure the vertical plantar pressure of a specific underfoot area. Of course, additional types of sensors which provide various information about dynamics of human locomotion may be used. For a given application, the use of sensors (22A, 22B, 24A, 24B, 26) is not restricted to a specific type of sensor, multiple types of sensors in various combinations may be used.

As illustrated in FIG. 1, the sensors (22A, 22B), may comprise localized plantar pressure sensors located at spaced locations on the prosthetic foot (20) to measure the vertical plantar pressure of a specific underfoot area. Similarly, the plantar pressure sensors (24A, 24B) located on the side of the healthy foot may be provided at spaced locations in a custom-made insole, preferably in the form of a standard orthopaedic insole, that is modified to embed the two sensors (24A, 24B) for the measurement of two localized plantar pressures. The sensors (22A, 22B, 24A, 24B) are operable to measure the weight transfer along the foot as the individual moves which may be combined with other sensors (26) such as kinematic sensors to measure the angular speed of body segments of the lower extremities and kinematic sensors to measure the angle of the prosthesis (14) knee joint.

Each sensor (22A, 22B, 24A, 24B) may comprise a thin Force-Sensing Resistor (FSR) polymer cell directly connected to the interface (30) of the control system (100) or indirectly using an intermediary system (not shown), for instance a wireless emitter. Of course, other types of communication link technologies may be used, such as, for example, optical. The FSR cell has a decreasing electrical resistance in response to an increasing force applied perpendicularly to the surface thereof. Each cell outputs a time variable electrical signal for which the intensity is proportional to the total vertical plantar pressure over its surface area. The size and position of the plantar pressure sensors (22A, 22B, 24A, 24B) may be defined in accordance with the stability and the richness (intensity) of the localized plantar pressure signals provided by certain underfoot areas during locomotion. For example, it was found by experimentation that the heel and the toe regions are two regions of the foot sole where the Plantar Pressure Maximum Variation (PPMV) may be considered as providing a signal that is both stable and rich in information.

Accordingly, the controller (40) may use the data signals from the four localized plantar pressure sensors (22A, 22B, 24A, 24B), as well as the information gathered from the data signals of the other sensors (26) such as kinematic sensors, in order to decompose the locomotion of the individual (10) into a finite number of states, and generate the appropriate control signals for controlling the actuating mechanism (16) according to the locomotion. Of course, the controller (40) is not limited to the use of the preceding data signals.

An example of a controller (40) and control system (100) using sensors comprising plantar pressure sensors as well as kinematic sensors is described in U.S. patent application Ser. No. 10/600,725 filed Jun. 20, 2003, entitled "CONTROL SYSTEM AND METHOD FOR CONTROLLING AN ACTUATED PROSTHESIS", by Stephane Bedard, the entire disclosure of which is hereby incorporated by reference herein.

Figure 3:
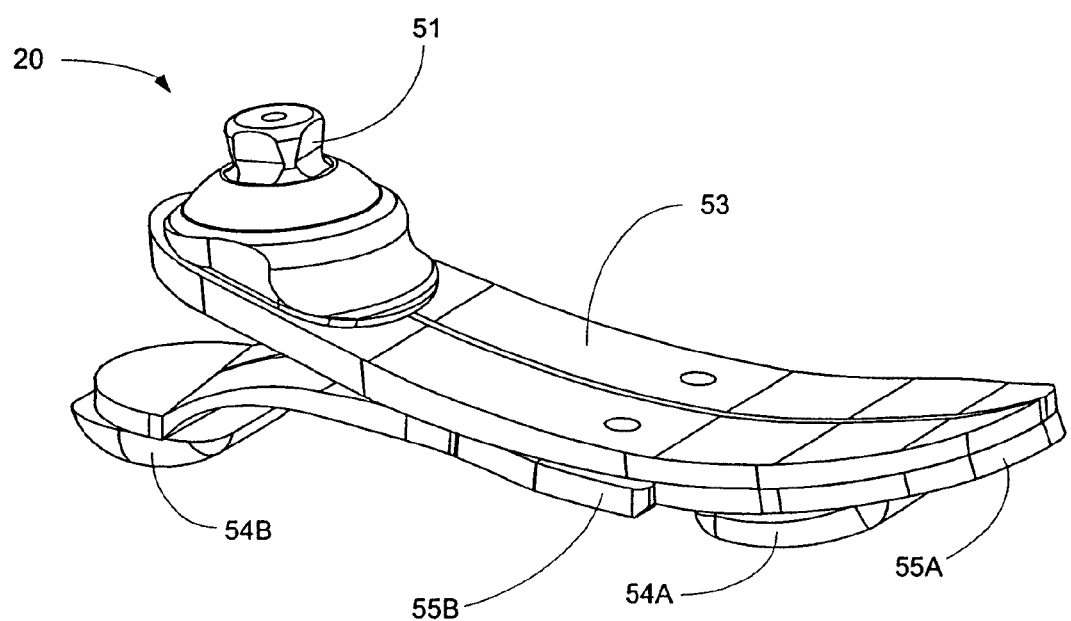
FIG. 3 is a perspective view, from the front and slightly above, of a instrumented prosthetic foot.
Figure 4:
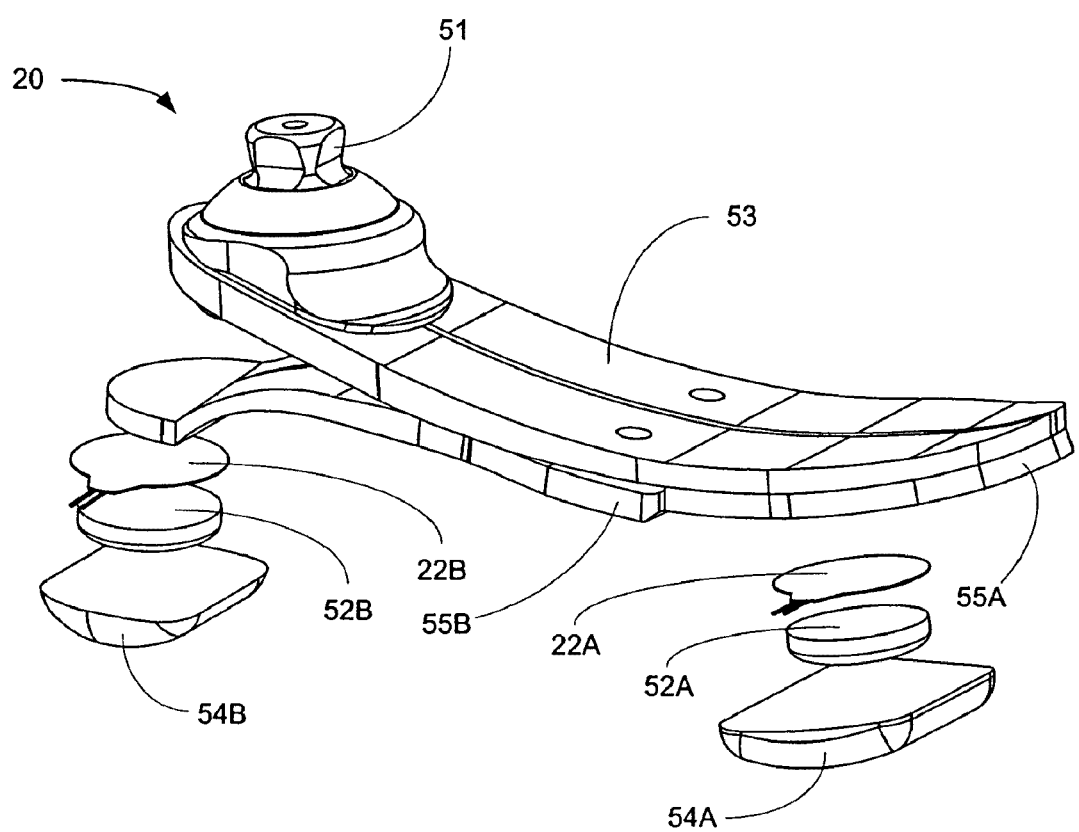
FIG. 4 is an exploded perspective view of the instrumented prosthetic foot of FIG. 3.

To facilitate the acquisition of the data in a repeatable and dependable manner, the sensors (22A, 22B) are incorporated in to the structure of the foot (20). An embodiment of the instrumented prosthetic foot (20) is shown in more detail in FIGS. 3 and 4. The instrumented prosthetic foot (20) includes a foot plate (53), forming an elongated body, with a connector (51) at one end, a toe plate (55A) and a heel plate (55B) that is cantilevered from the foot plate (53). Such an arrangement is provided by, for example, a Vari-Flex® prosthetic foot from Össur. Pressure sensors (22A, 22B) are located at longitudinally spaced locations on the underside of the foot plate (53) and heel plate (55) respectively. The sensors (22A, 22B) are covered by rigid plates (52A, 52B) and resilient pads (54A, 54B). The pressure sensors (22A, 22B) are located so as to be responsive to loads imposed on the instrumented prosthetic foot (20) at the regions corresponding to the toe area and the heel area respectively.

The rigid plates (52A, 52B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

The pads (54A, 54B) wrap up the rigid plates (52A, 52B) and the sensors (22A, 22B), forming a ground engaging member, in order to optimize the contact between the instrumented prosthetic foot (20) and the ground. The pads (54A, 54B) may be made of 40 A durometer polyurethane. Of course, other type of material may be used as well.

In operation, therefore, as the foot (20) traverses the ground, the force applied to the heel plate (55B) is measured by the sensor (22B) and a corresponding signal forwarded to the controller (40). The force applied to the toe plate (55A) is also measured by the sensor (22A) and the relative loading between the two locations is measured. As the foot (20) continues to traverse the ground, the force applied to the toe area increases and that at the heel decreases to provide a pair of signals from which the disposition of the leg may be determined and the appropriate control provided to the actuator (16).

Figure 5:
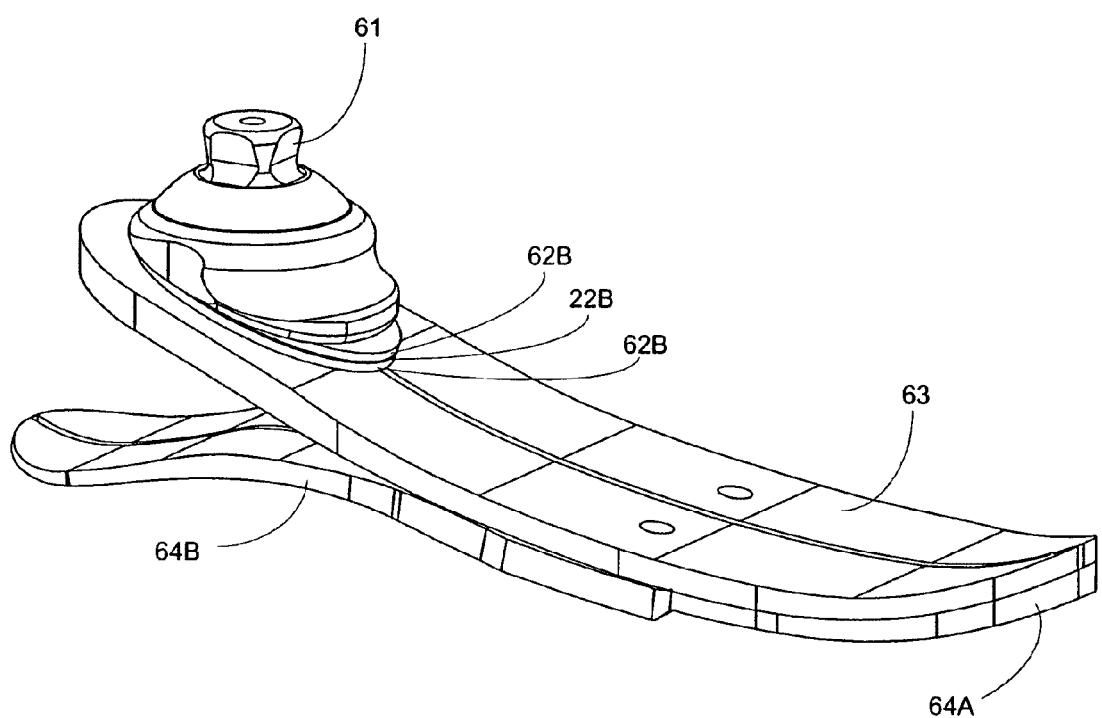
FIG. 5 is a perspective view, from the front and slightly above, of an alternative embodiment of the instrumented prosthetic foot of FIG. 3.
Figure 6:
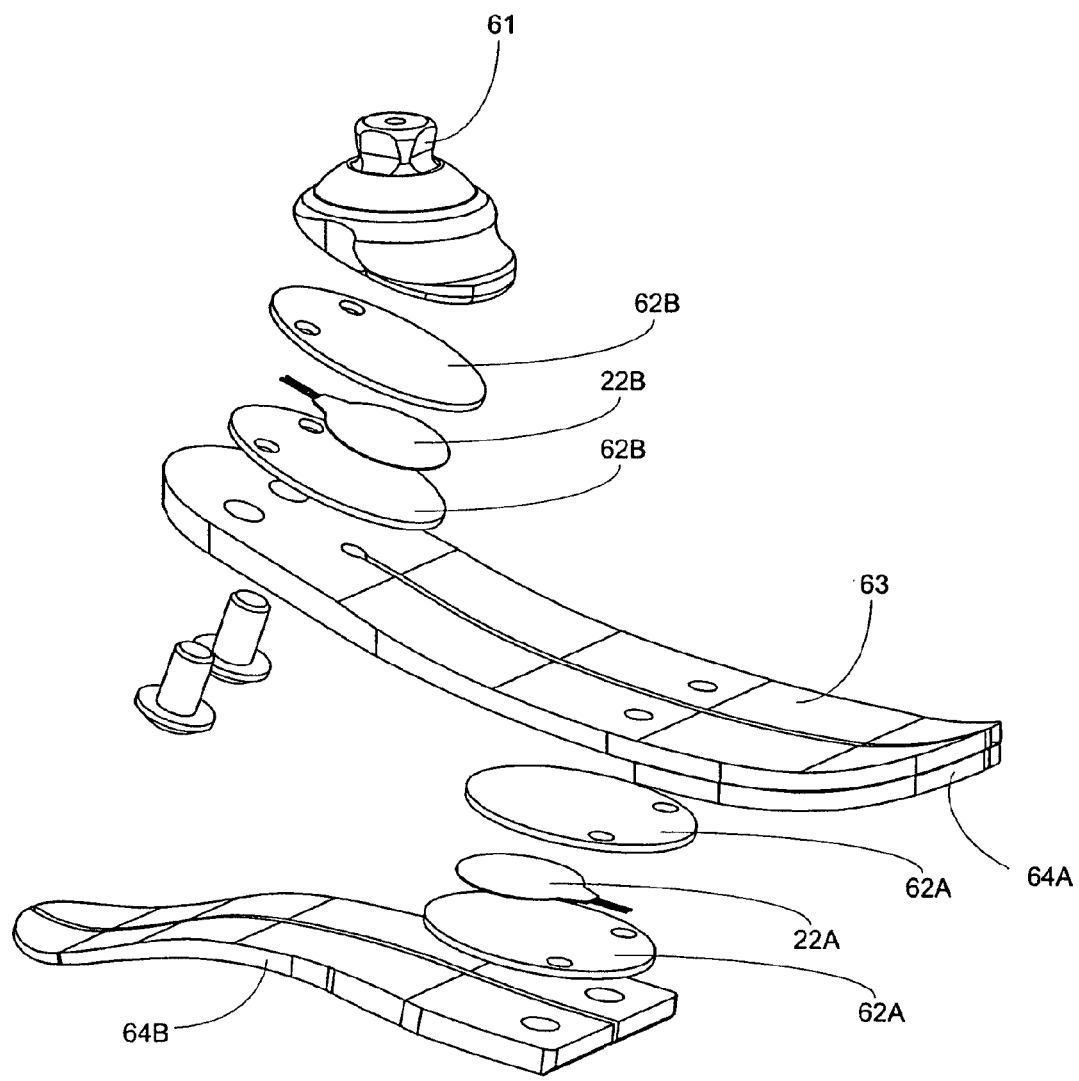
FIG. 6 is an exploded perspective view of the instrumented prosthetic foot of FIG. 5.

An alternative embodiment of the instrumented prosthetic foot (20) is shown in FIGS. 5 and 6. The instrumented prosthetic foot (20) includes connector (61), foot plate (63), toe plate (64A) and heel plate (64B), such as provided by, for example, a Vari-Flex® prosthetic foot from Össur. Pressure sensors (22A, 22B) are located between the foot plate (63) and rigid plates (62A, 62B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (62A), which in turn are positioned between the heel plate (64B) and the foot plate (63). Pressure sensor (22B) is sandwiched between a pair of rigid plates (62B), which in turn are positioned between the foot plate (63) and the connector (61).

As for the previous embodiment, rigid plates (62A, 62B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

Figure 7:
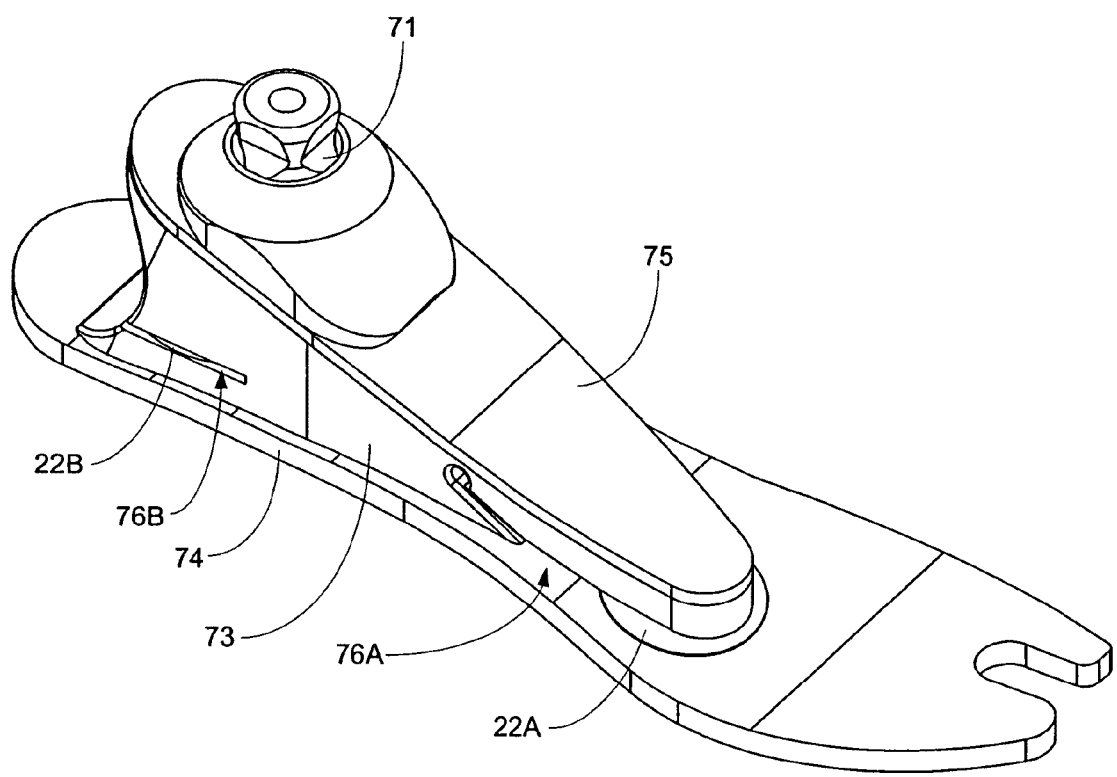
FIG. 7 is a perspective view, from the front and slightly above, of another alternative embodiment of the instrumented prosthetic foot of FIG. 3
Figure 8:
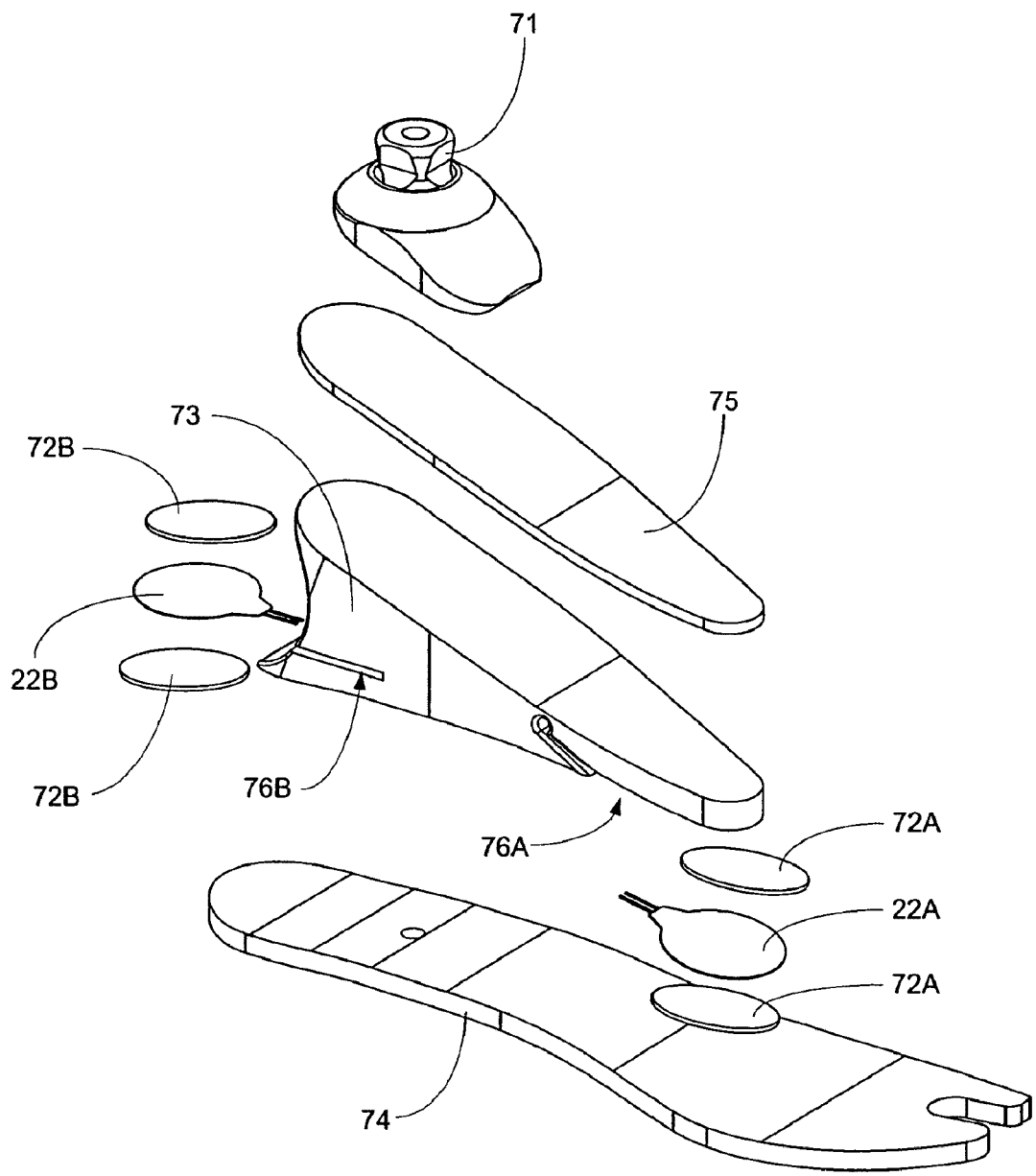
FIG. 8 is an exploded perspective view of the instrumented prosthetic foot of FIG. 7.

Another alternative embodiment of the instrumented prosthetic foot (20) is shown in FIGS. 7 and 8. The instrumented prosthetic foot (20) includes connector (71), top foot plate (75), foam cushion core (73) and bottom foot plate (74), such as provided by, for example, a LP Talux® prosthetic foot from Össur. Pressure sensors (22A, 22B) are sandwiched between pairs of rigid plates (72A, 72B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (72A), which in turn are positioned within gap (76A), which is located between a bottom foot plate (74) and a foam cushion core (73). Pressure sensor (22B) is sandwiched between a pair of rigid plates (72B), which in turn are positioned within gap (76B), which is located within the foam cushion core (73).

Again, as for the previous embodiments, rigid plates (72A, 72B) covering the sensors (22A, 22B), although not essential, help to optimize the pressure distribution on the entire surface of the sensors (22A, 22B) as well as preventing any shearing and may be made of 85 A durometer polyurethane. Of course, other type of material may be used as well.

Figure 9:
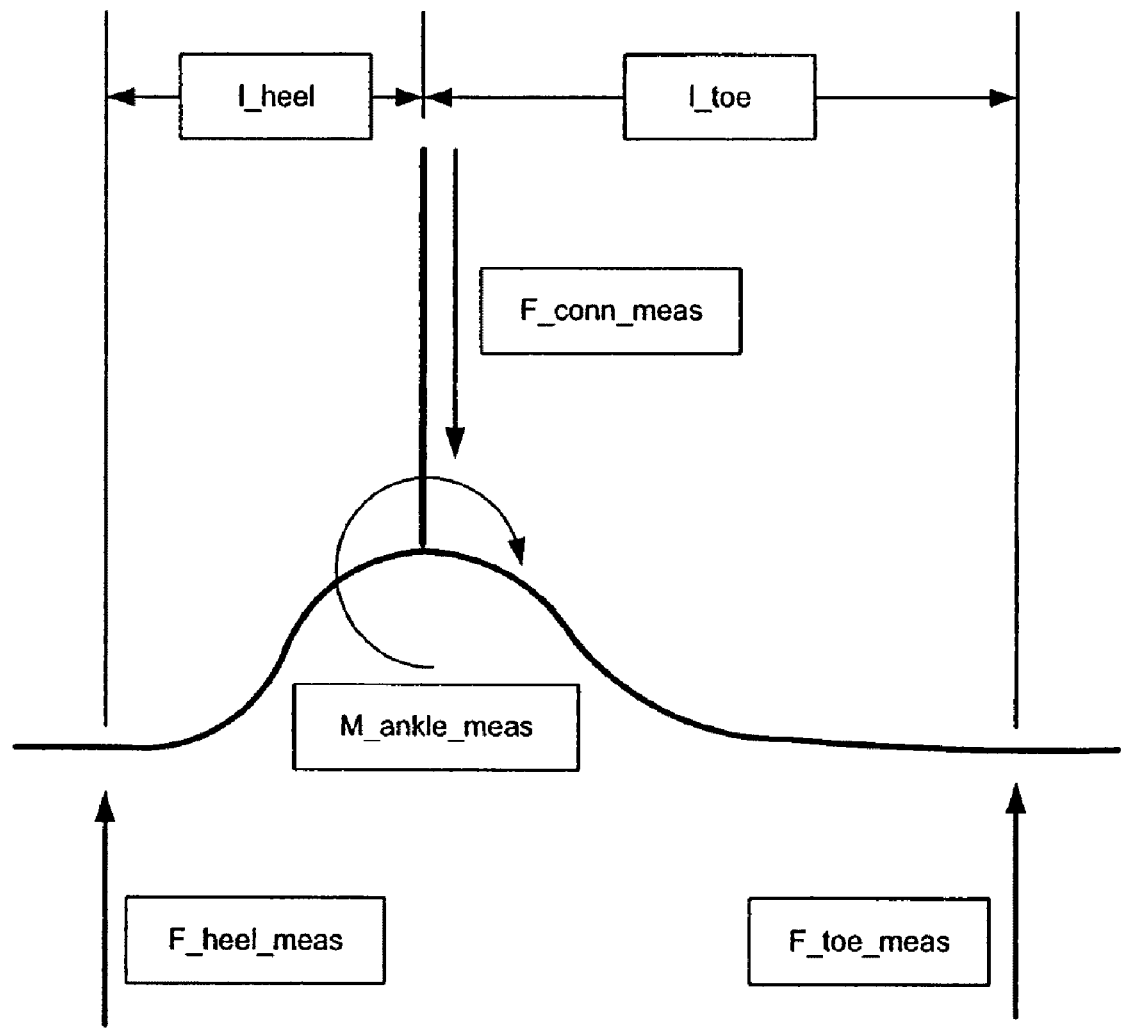
FIG. 9 is schematic view of forces exerted on a foot.

In the previous embodiments, the force (or pressure) at the toe and heel areas, F_toe and F_heel respectively, was obtained by positioning pressure sensors (22A, 22B) directly at those areas. More specifically, referring to FIG. 9, F_toe and F_heel were obtained as follows:

$$F\_toe = F\_toe\_meas \qquad \text{Equation 1}$$

$$F\_heel = F\_heel\_meas \qquad \text{Equation 2}$$

In other possible embodiments of the instrumented prosthetic foot (20), sensors (22A, 22B) may not be restricted to being positioned directly at the toe and heel areas, the equivalent information may be obtained by measuring the equivalent torque at the ankle and the axial force at the connector of the instrumented prosthetic foot (20). F_toe and F_heel may be defined in terms of the torque measured at the ankle, M_ankle_meas, and the force measured at the connector, F_conn_meas, using the following equations:

$$F\_toe = \frac{M\_ankle\_meas + (F\_conn\_meas \cdot I\_heel)}{(I\_heel + I\_toe)} \qquad \text{Equation 3}$$

$$F\_heel = \frac{-M\_ankle\_meas + (F\_conn\_meas \cdot I\_toe)}{(I\_heel + I\_toe)} \qquad \text{Equation 4}$$

where
I_heel is the distance between the center of the connector and the center of the heel area;
I_toe is the distance between the center of the connector and the center of the toe area.

Figure 10:
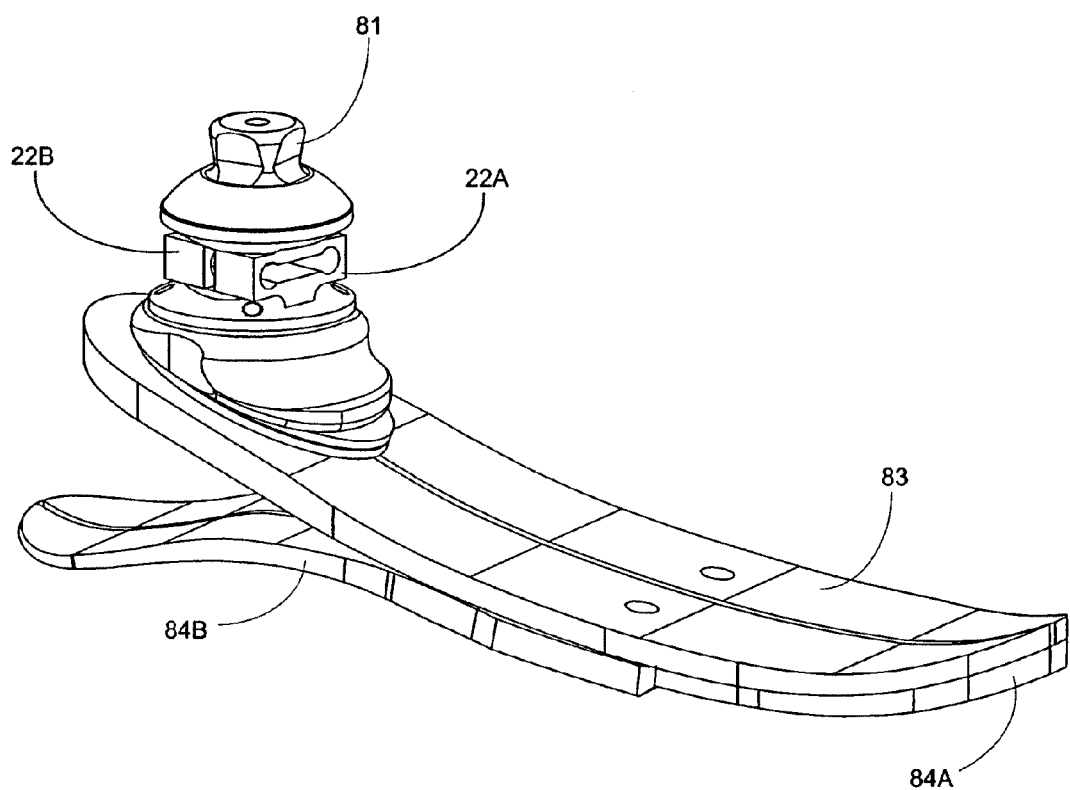
FIG. 10 is a perspective view, from the front and slightly above, of a further still alternative embodiment of the instrumented prosthetic foot of FIG. 3
Figure 11:
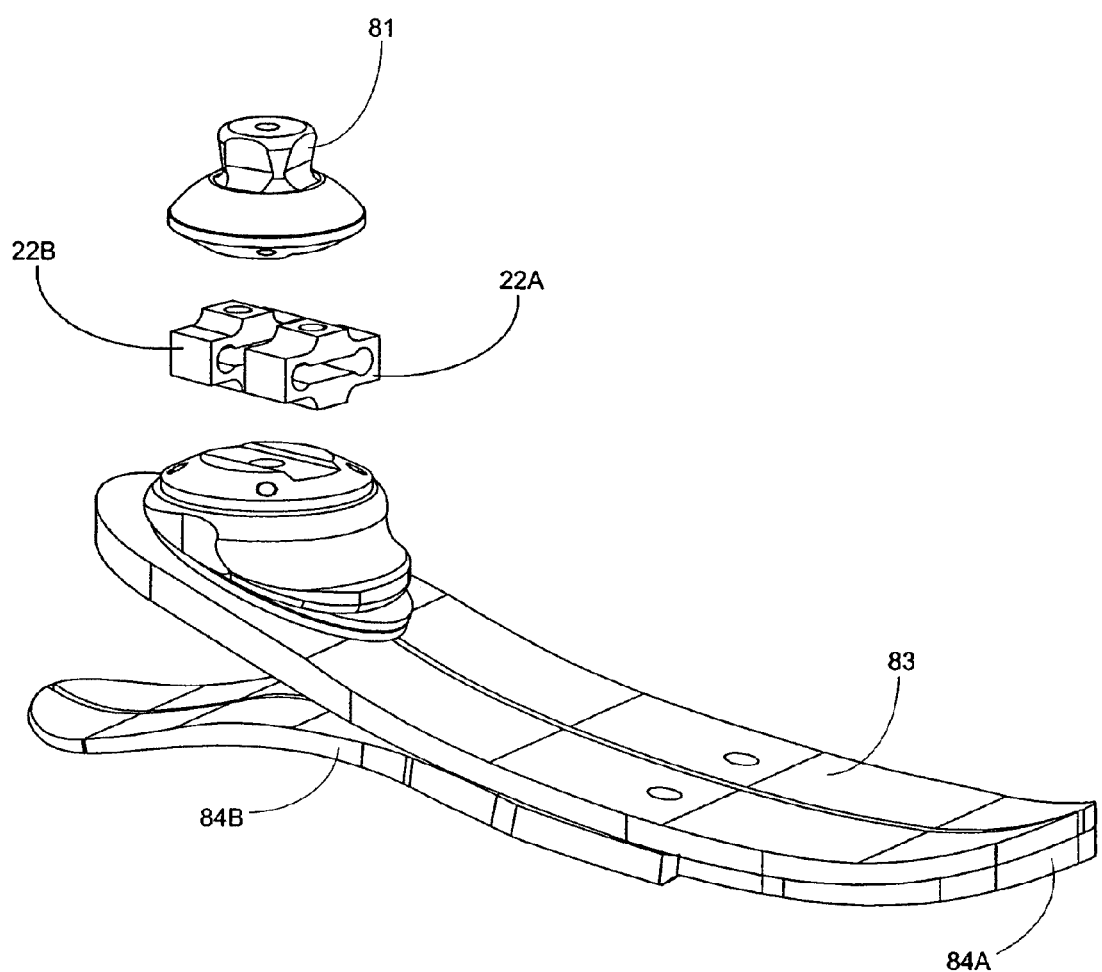
FIG. 11 is an exploded perspective view of the instrumented prosthetic foot of FIG. 10.

Following the previous discussion about the locations of sensors (22A, 22B), a further alternative embodiment of the instrumented prosthetic foot (20) is shown in FIGS. 10 and 11. The instrumented prosthetic foot (20) includes connector (81), foot plate (83), toe plate (84A) and heel plate (84B), such as provided by, for example, a Vari-Flex® prosthetic foot from Össur, and load cells (22A, 22B). Load cells (22A, 22B) are located below connector (91), load cell (22A) being slightly biased towards the toe area of the foot and load cell (22B) being slightly biased towards the heel area. Since the sensors (22A, 22B) are not located directly at the toe and heel areas, Equation 3 and Equation 4 may be used, for example by controller (40), to compute the equivalent pressures at the toe and heel areas by defining the equivalent torque at the ankle and the axial force at connector (81) as follows:

$$F\_conn\_meas = F\_22B + F\_22A \qquad \text{Equation 5}$$

$$M\_ankle\_meas = F\_22B \cdot I\_22B - F\_22A \cdot I\_22A \qquad \text{Equation 6}$$

Where
F_22B is the force measured at sensor 22B;
F_22A is the force measured at sensor 22A;
I_22B is the distance between the center of the connector (81) and the center of sensor 22B;
I_22A is the distance between the center of the connector (81) and the center of sensor 22A.

Figure 12:
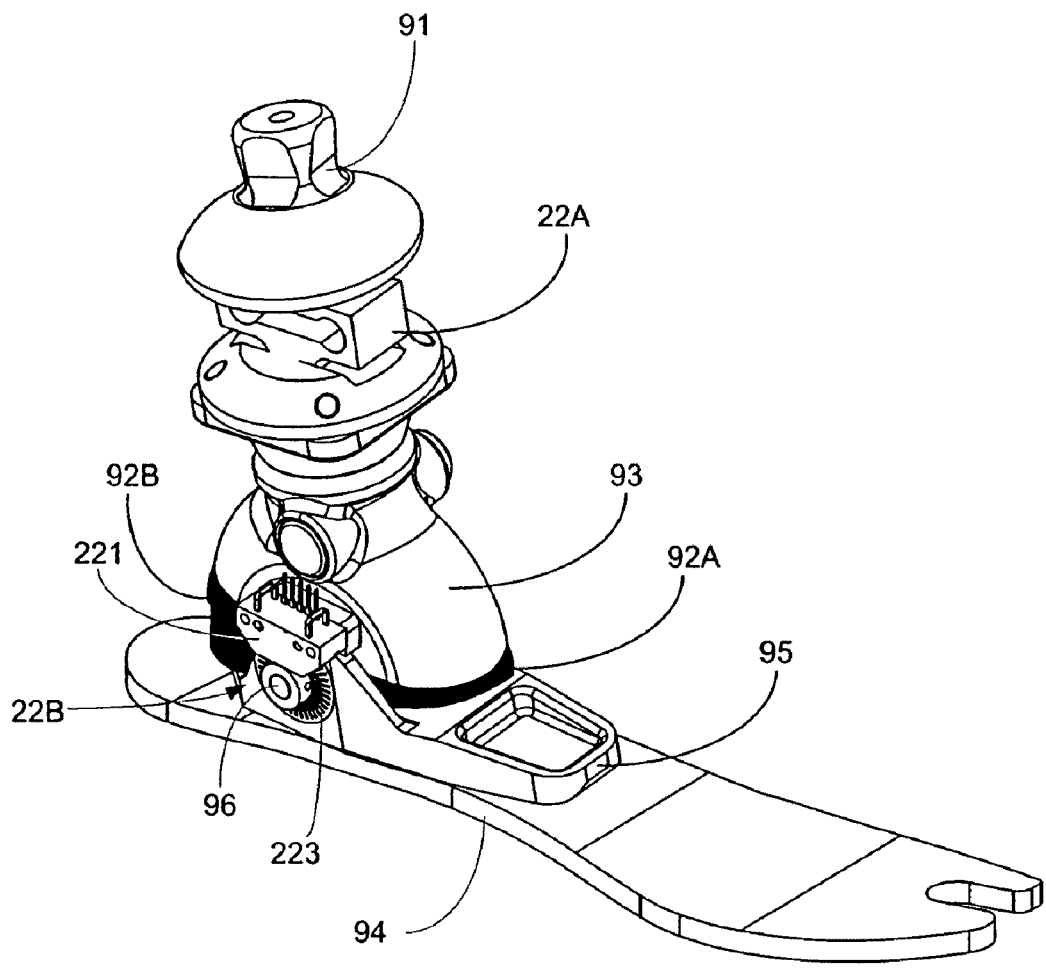
FIG. 12 is a perspective view, from the front and slightly above, of a yet further still alternative embodiment of the instrumented prosthetic foot of FIG. 3
Figure 13:
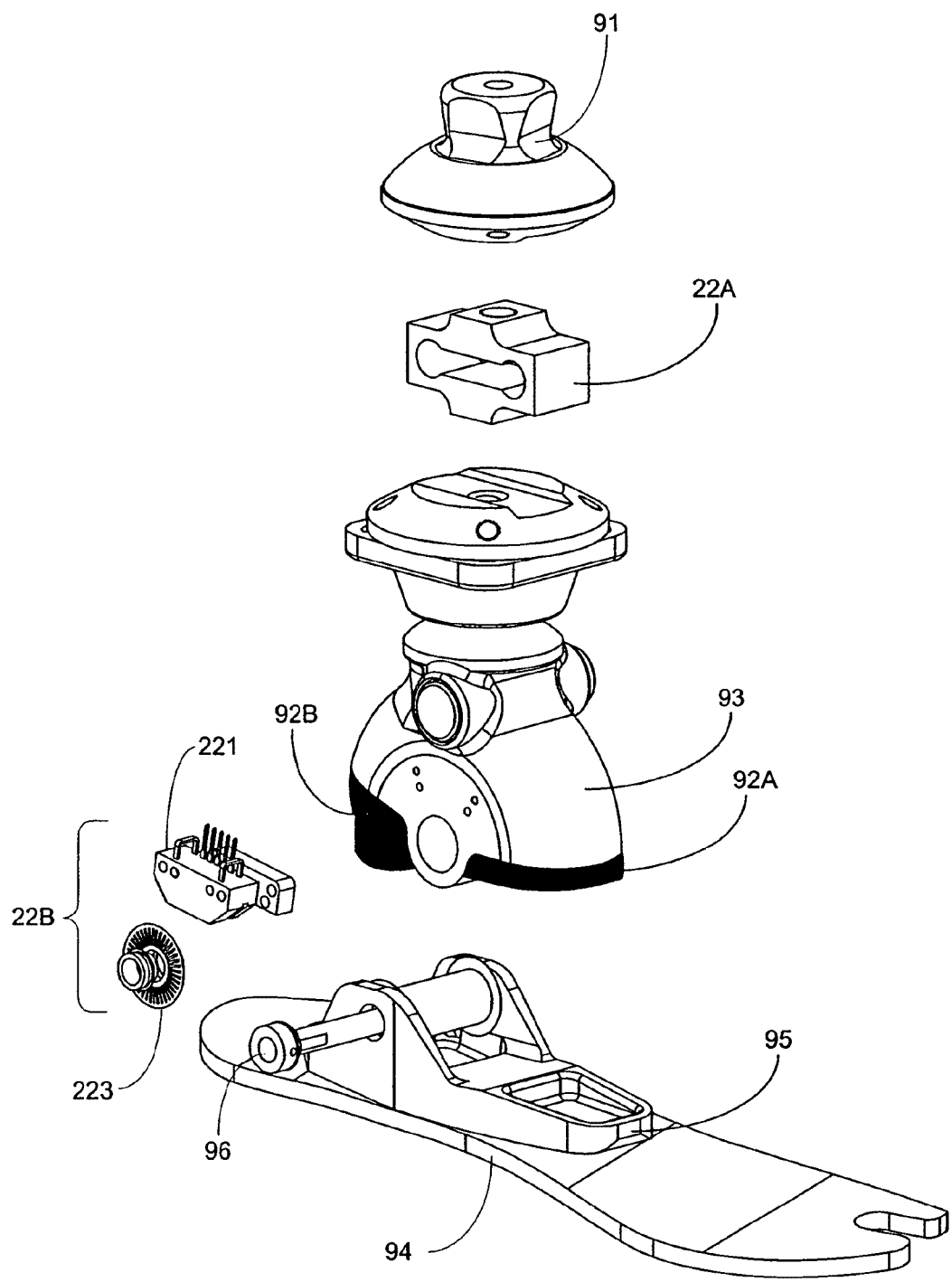
FIG. 13 is an exploded perspective view of the instrumented prosthetic foot of FIG. 12.

In the previous embodiments of the instrumented prosthetic foot (20), the force (or pressure) at the toe and heel areas, F_toe and F_heel respectively, was obtained either by positioning pressure sensors (22A, 22B) directly at those areas or by positioning pressure sensors or load cells (22A, 22B) in other areas and obtaining the equivalent information by computing the equivalent torque at the ankle and the axial force at the connector. Other types of sensors may also be used to obtain the equivalent torque at the ankle and the axial force at the connector. Such an example is illustrated by a further still embodiment of the instrumented prosthetic foot (20), which is shown in FIGS. 12 and 13. The instrumented prosthetic foot (20) includes connector (91), mounted on pivoting ankle (93). Bumpers (92A, 92B) are positioned between the pivoting ankle (93) and rocker plate (95) located on a foot plate (94). The pivoting ankle (93) is connected to the rocker plate (95) by a pivot pin (96). Such an arrangement is provided by, for example, an Elation® prosthetic foot from Össur. A load cell (22A) and an optical encoder (22B) are incorporated into the foot (20) to provide measurement of the distribution of forces along the foot (20). Load cell (22A) is positioned between connector (91) and pivoting ankle (93). Optical encoder (22B) comprises reader (221) and disk (223). Reader (221) is located on pivoting ankle (93) while disk (223) is located on rocker plate (95) and encircles pivot pin (96). Once again, Equation 3 and Equation 4 may be used, for example by controller (40), to compute the equivalent pressures at the toe and heel areas by defining the equivalent torque at the ankle and the axial force at connector (91) as follows:

$$F\_conn\_meas = F\_22A \qquad \text{Equation 7}$$

$$M\_ankle\_meas = R\_ankle\_meas \cdot R\_const \qquad \text{Equation 8}$$

Where
F_22A is the force measured at sensor 22A;
R_ankle_meas is the rotation measurement of pivoting ankle (93) about pivot pin (96) as measured by optical encoder (22B);
R_const is a constant associated with the resistance of bumpers (92A, 92B) to compression, which constant varies depending in the material used.

Figure 14:
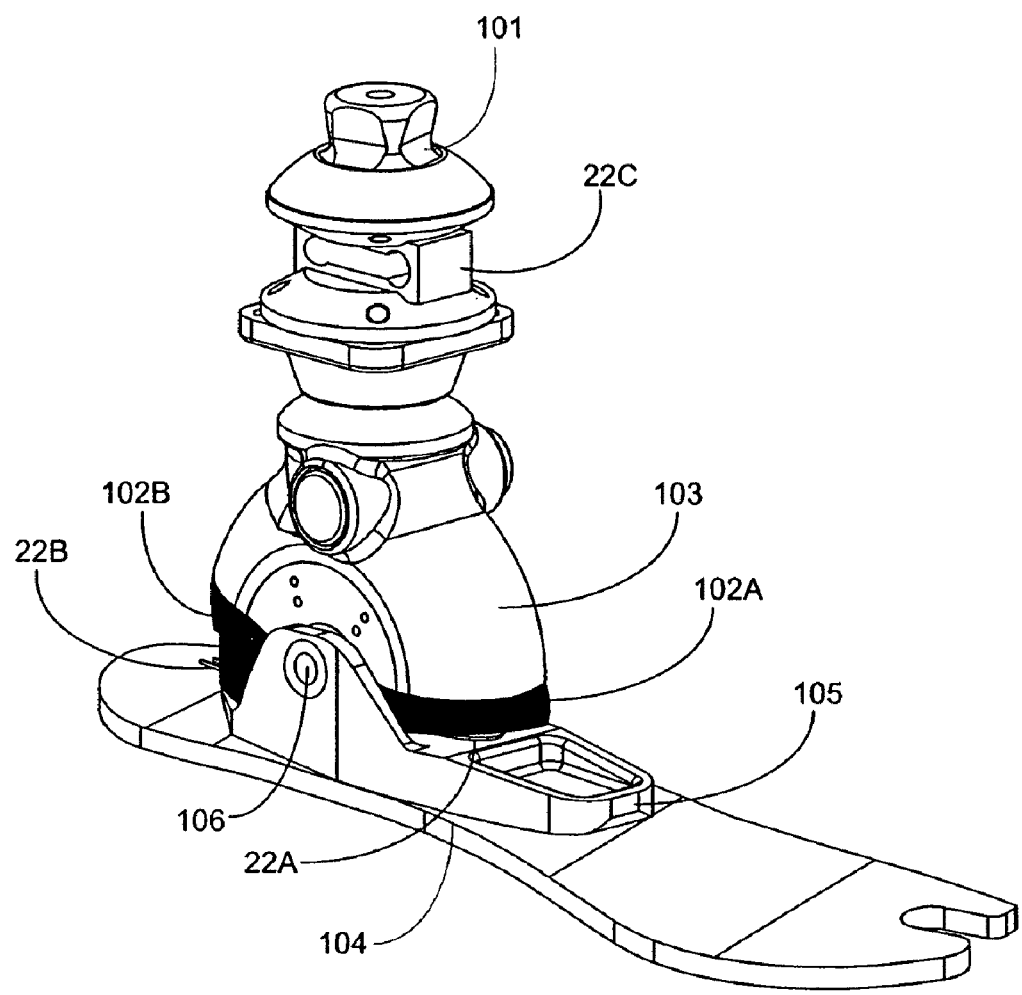
FIG. 14 is a perspective view, from the front and slightly above, of a further alternative embodiment of the instrumented prosthetic foot of FIG. 3
Figure 15:
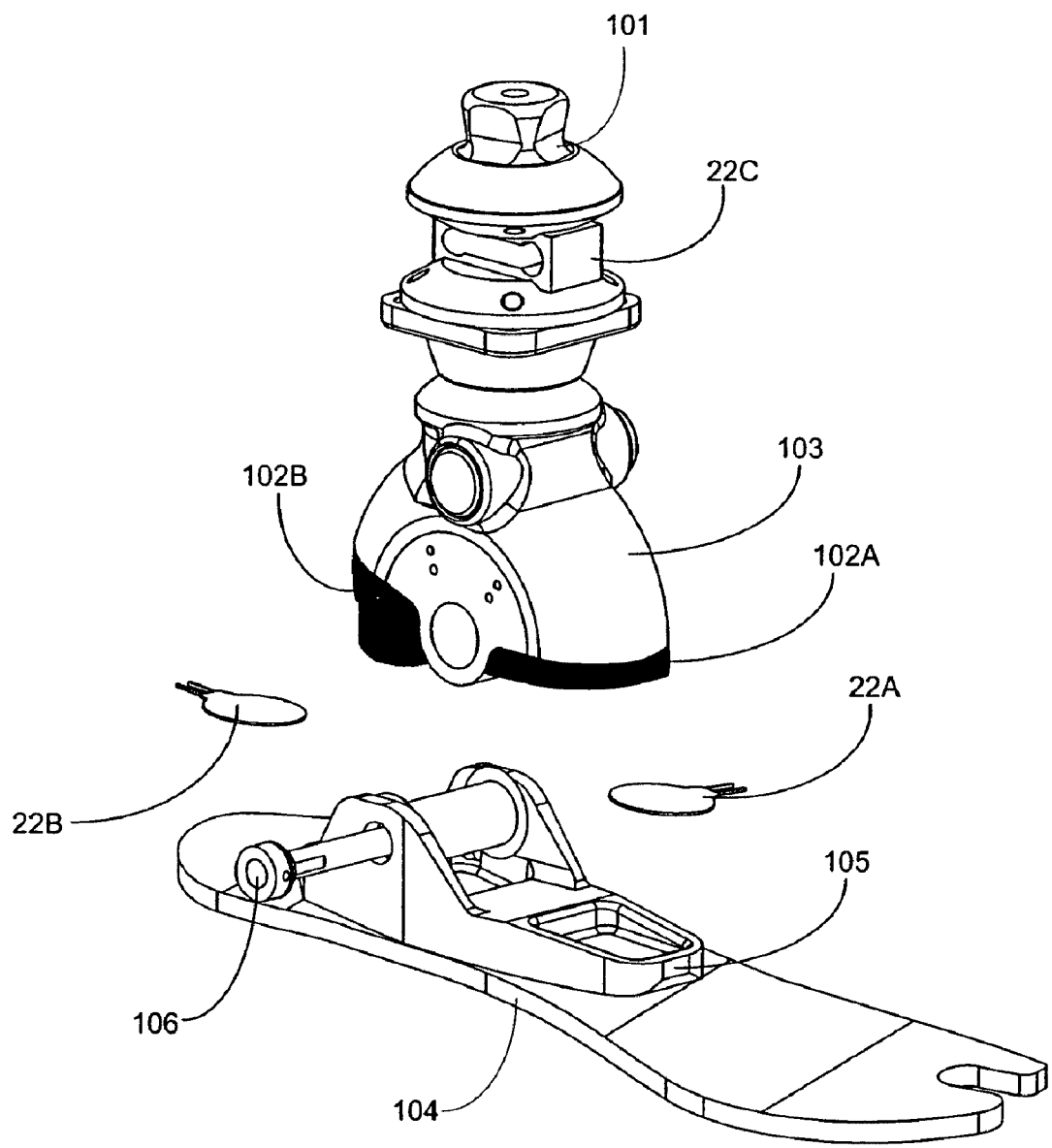
FIG. 15 is an exploded perspective view of the instrumented prosthetic foot of FIG. 14.

A yet further alternative embodiment of the instrumented prosthetic foot (20) is shown in FIGS. 14 and 15. The instrumented prosthetic foot (20) includes connector (101), mounted on pivoting ankle (103). Bumpers (102A, 102B) are positioned between the pivoting ankle (103) and rocker plate (105) located on a foot plate (104). The pivoting ankle (103) is connected to the rocker plate (105) by a pivot pin (106). Such an arrangement is provided by, for example, an Elation® prosthetic foot from Össur. Pressure sensors (22A, 22B) and load cell (22C) are incorporated into the foot (20) to provide measurement of the distribution of forces along the foot (20). Pressure sensor (22A) is positioned between rocker plate (85) and bumper (82A) while pressure sensor (22B) is positioned between rocker plate (85) and bumper (82B). A load cell (22C) is positioned between connector (91) and pivoting ankle (93).

In this embodiment, Equation 6 is used to compute the equivalent torque at the ankle, while the axial force at connector (101) is computed using the following equation:

$$F\_conn\_meas = F\_22C \qquad \text{Equation 9}$$

Load cell (22C) is required to compute the axial force at connector (101) since when there is no torque at the ankle, i.e. the wearer of the prosthesis is standing still, the axial force is being exerted in its entirety onto pivot pin (96).

In all of the described embodiments, the sensors (22A, 22B) may be directly connected to interface (30) of control system (100) or indirectly using an intermediary system (not shown), for instance a wireless emitter. Of course, other types of communication link technologies may be used, such as, for example, optical.

Other types of non-articulated or articulated prosthetic foot may be used as well as long as the selected prosthetic foot provides approximately the same dynamical response as the ones mentioned here above. Nevertheless, an articulated foot offers the best performances. The instrumented prosthetic foot (20) may further have an exposed metal or composite structure or it may have a cosmetic covering that gives it the appearance of a human ankle and foot.

It should be noted that the present invention is not limited to its use with the mechanical configuration illustrated in FIG. 1 or the control system (100) illustrated in FIG. 2. It may be used with a leg prosthesis having more than one joint. For instance, it may be used with a prosthesis having an ankle joint, a metatarsophalangeal joint or a hip joint in addition to a knee joint. Moreover, instead of a conventional socket a osseo-integrated devices could also be used, ensuring a direct attachment between the mechanical component of the prosthesis and the amputee skeleton. Other kinds of prostheses may be used as well.

What is claimed is:

1. A prosthetic foot and ankle system, comprising:
   a prosthetic foot comprising at least one elongated foot plate having a toe region and a heel region;
   an ankle structure pivotally connected to the elongated foot;
   a pyramid connector mounted to the ankle structure to operably connect the prosthetic foot and ankle system to a user;
   an ankle encoder positioned on the ankle structure about its pivot axis configured to measure the rotation of the ankle structure about its pivot axis;
   a sensor positioned on the ankle structure configured to measure pressure or force caused by the prosthetic foot interacting with the ground; and
   a controller configured to receive data from the ankle encoder and the sensor and configured to determine the torque at the ankle structure using the received data.

2. A prosthetic foot and ankle system according to claim 1, wherein the sensor is configured to measure an axial pressure or force.

3. A prosthetic foot and ankle system according to claim 1, further being associated with an active actuator controlled by the controller.

4. A prosthetic foot and ankle system according to claim 1, wherein the controller is further configured to determine the pressure or force at the connector using the received data.

5. A prosthetic foot and ankle system according to claim 1, wherein the ankle encoder and the sensor transmit signals to the controller using a wired connection.

6. A prosthetic foot and ankle system according to claim 1, wherein the ankle encoder and the sensor transmit signals to the controller using a wireless connection.

7. A prosthetic foot and ankle system according to claim 1, wherein the sensor is a load cell.

\* \* \* \* \*